United States Patent [19]
Feuer et al.

[11] 3,949,085
[45] *Apr. 6, 1976

[54] ANABOLIC-WEIGHT-GAIN PROMOTING COMPOSITIONS CONTAINING ISOFLAVONE DERIVATIVES AND METHOD USING SAME

[75] Inventors: László Feuer; Mihály Nogradi; Agnes Gottsegen; Borbala Vermes; Janos Streliszky; Andreas Wolfner; Lorant Farkas; Sandor Antus; Maria Kovaks, all of Budapest, Hungary

[73] Assignee: Chinoin Gyogyszer-es Vegyeszeti Termakek Gyarart, Budapest, Hungary

[ * ] Notice: The portion of the term of this patent subsequent to Sept. 3, 1991, has been disclaimed.

[22] Filed: Aug. 15, 1974

[21] Appl. No.: 497,644

Related U.S. Application Data

[60] Division of Ser. No. 371,560, June 19, 1973, Pat. No. 3,907,830, which is a continuation-in-part of Ser. No. 146,773, May 25, 1971, Pat. No. 3,833,730.

[30] Foreign Application Priority Data
May 27, 1970   Hungary ........................... CI 996

[52] U.S. Cl. ................................................ 424/283
[51] Int. Cl.² ........................................ A61K 31/35
[58] Field of Search ..................................... 424/283

[56] References Cited
UNITED STATES PATENTS
3,833,730   9/1974   Feuer ................................ 424/283

*Primary Examiner*—Sam Rosen
*Attorney, Agent, or Firm*—Karl F. Ross; Herbert Dubno

[57] ABSTRACT

A method of anabolic treatment in humans comprises administering a compound of the following formula:

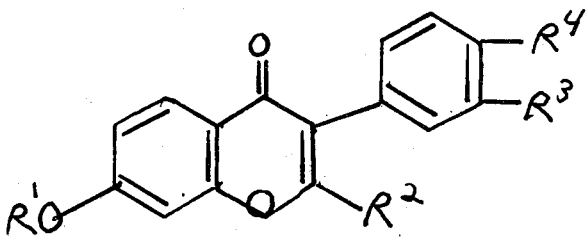

wherein R is halosubstituted, nitrosubstituted, or unsubstituted benzyl, $R^2$ is hydrogen, methyl or carboxy, and $R^3$ and $R^4$ are hydrogen, methoxy or nitro. Pharmaceutical compositions are also disclosed.

10 Claims, No Drawings

ANABOLIC-WEIGHT-GAIN PROMOTING COMPOSITIONS CONTAINING ISOFLAVONE DERIVATIVES AND METHOD USING SAME

RELATED APPLICATIONS

This application is a division of co-pending application U.S. Ser. No. 371,560 filed 19 June 1973, now U.S. Pat. No. 3,907,830 which in turn is a continuation-in-part of U.S. Ser. No. 146,773 filed 25 May 1971, (now U.S. Pat. No. 3,833,730).

FIELD OF THE INVENTION

The present invention relates to metabolic compounds and, more particularly, to anabolic compounds having weight gain promoting effectiveness. The invention also relates to a method of treatment using these compounds and to treatment compositions incorporating same.

BACKGROUND OF THE INVENTION

In order to reduce protein deficiency in nutrition or to terminate it, thorough and significant research is being carried out throughout the world. One of the most obvious ways to achieve this objective is the use of additives to nutrients and feed which improve the utilization of the nutrients introduced into the organism. In animal husbandry, these additives result in a higher body-weight increase for an identical feed consumption and breeding period.

However, it has been rather difficult to develop an appropriate substance for increasing animal body weight since the use of substances with hormonal effects and of antibiotics is not permitted in most of the countries.

Isoflavone compounds have been subjected to a detailed investigation from the aspect of their body-weight increasing effect. These compounds are rather widespread in plants, and a great number of them show oestrogenic properties. (cf. Virtanen, A. J.: Angew. Chem. 30, 544, (1958); Virtanen, A. J., Hietala, P. K.: Acta Chem. Scand. 12, 579, (1958). Grazing animals become infertile on consuming certain varieties of clover; research into this problem has shown that genistein and daidzein present in the plants consumed by pasturing animals are responsible for this effect because of their marked oestrogenic action (Chang, E. W. et al.: Ann. N.Y. Acad. Sci. 61, 625, 1955).

For the determination of the oestrogenic effect of isoflavones a reliable method has been evolved by East, J. (J. Endocrin. 13, 94, 1955). Since that time a number of authors have dealt very thoroughly with this problem (Matrone, G. et al.: Nutrition 59, 235, 1956; Gabor, M.: Naturwise. 46½ 650, 1959; Crabb, P. et al.: J. Am. Chem. Soc. 85, 5258, 1958).

DISCLOSURE OF PARENT APPLICATION

The prior application relates to an animal feed containing as an active ingredient at least one compound of the formula

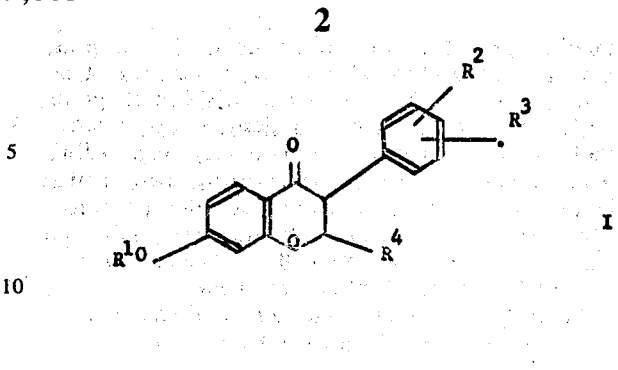

or a salt thereof, in which $R^1$ represents an unsubstituted or substituted and/or unsaturated alkyl group, $R^2$, and $R^3$ represent hydrogen, an alkoxy, nitro, halogen, sulpho or hydroxy group, and $R^4$ is hydrogen, an alkyl or —COOH group.

The metabolic composition can be favorably applied as a feed additive. In that case one of the compounds of formula I, or thereof, is added to the feed in amounts from 0.00002 to 0.1%, prior to or after the admixture of further additives.

The active ingredient may bear, if desired, also substituents on the alkyl group $R^1$. Substituents in this position may be a heterocyclic group, a dialkylamino group, carbethoxy, hydroxyalkyl, alkoxyalkyl or aryl or a substituted aryl group. The $R^1$ alkyl group may be substituted with a nitrogen containing heterocyclic group.

If desired, the compounds of the formula I are mixed with further additives. Substances with biological activity such as vitamins, amino acids, choline chloride, salts of mineral acids, trace elements and other known substances of biological importance are suitable. The feed additive can be used in premixes, in admixture with other components possessing biological effects. As further additives various diluents, solvents, sliding and molding substances, and carriers may be used. The feed additive can be mixed with the feed as a powder, granulate, powder mixture, emulsion or suspension. It is also possible to use the feed composition in mixtures added to the drinking water of the animals.

The earlier application described compounds of the formula

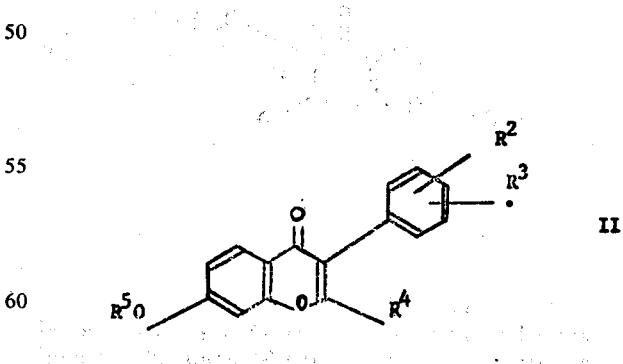

wherein $R^2$, $R^3$ and $R^4$ have the same definition as in formula I, while $R^5$ represents an unsaturated or saturated and/or substituted or unsubstituted alkyl group having a carbon chain of more than two carbon atoms and the salts of these compounds. The alkyl group represented by $R^5$ may bear, if desired, a substituent such as an aromatic or heteroaromatic ring, dialkylamino groups (such as dimethylamino, diethylamino groups), a carbethoxy group or alkoxy, alkyl or hydroxyalkyl groups. The heterocyclic ring preferably contains a nitrogen atom and an alkoxy, halogen, alkyl or —COOH group as a further substituent.

The new compounds of the formula II can be made by a process wherein ketones of the formula

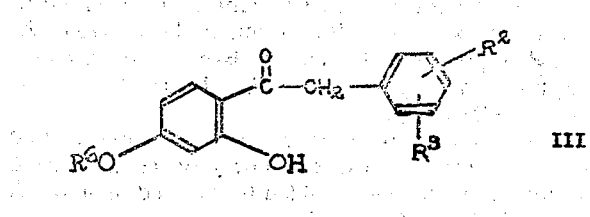 III a. are reacted with an alkyl orthoformate in the presence of a basic catalyst, or
b. are reacted with hydrogen cyanide and/or cyanides in the presence of hydrogen halide, or
c. are reacted with an alkyl formate in the presence of an alkali metal, or
d. are reacted with an alkyl oxalyl halogenide, followed, if desired, by saponification and/or decarboxylation of the obtained isoflavone ester, or
e. are reacted with an organic anhydride, or
f. are reacted with a N,N-dialkyl acid amide in the presence of phosphorus oxychloride.
g. In an alternative variant, 2-hydroxy-isoflavanone derivatives of the formula

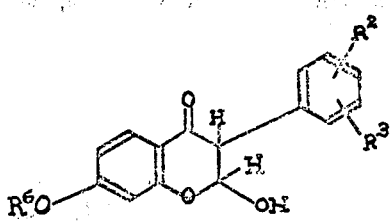 IV are dehydrated,
and finally, if necessary, the $R^6$ group is converted into an $R^5$ group and/or the compounds are converted into salts or respectively, liberated from their salts;
in the formula
$R^2$ and $R^3$ represent hydrogen, a halogen, alkoxy, nitro, sulpho or hydroxy group, $R^4$ is hydrogen, alkyl or —COOH group, $R^5$ an unsubstituted or substituted and/or unsaturated or saturated alkyl group with a carbon chain longer than two carbon atoms, $R^6$ is hydrogen, or a substituted alkyl group or acyl group.

In carrying out variant (a) of the process, the preferred method is to react an appropriately substituted ketone with an orthoformic ester in an aprotic solvent of higher boiling point. Pyridine, dimethyl formamide or diethyleneglycol dimethylether may be used as solvents, while preferably piperidine, morpholine, pyrrolidine and other secondary amines may serve as basic catalysts.

In carrying out variant (b), the preferred method is to react the ketones with hydrogen cyanide, in an aprotic solvent, in the presence of dry gaseous hydrochloric acid or off nonbasic nature, preferably diethylether or other dialkylethers can be used. Zinc chloride or other Lewis acids may be used as catalysts. The reaction is carried out with hydrogen cyanide or with one of its appropriate salts, preferably with zinc cyanide. The mixture may be saturated with dry gaseous hydrochloric acid, and lastly, the formed substituted-form-imino-2-hydroxy-phenyl-benzyl-ketone hydrochlorides are decomposed by treatment with water.

In carrying out variant (c) of the process according to the invention, ketones of the formula

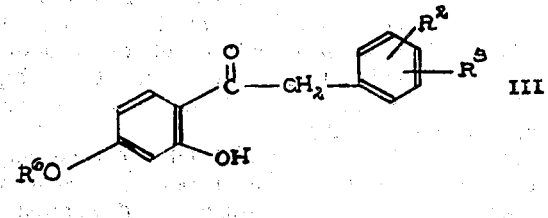 III are reacted with alkyl formates in the presence of an alkali metal. A preferred method is to dissolve an appropriately substituted 2-hydroxy-phenyl-benzyl-ketone in ethyl formate, and adding the solution dropwise to powdered sodium metal, then decomposing the reaction mixture with water, and separating the formed isoflavone.

According to variant (d) of the process, appropriately substituted 2-hydroxy-phenyl-benzyl ketones are reacted with alkyl oxalyl halides. The resulting 2-carbalkoxy-isoflavone derivative can be converted, if desired, into an isoflavone derivative unsubstituted in position 2, by hydrolysis of the ester group followed by decarboxylation. This process can be carried out preferably with methyl or ethyl oxalyl chloride in the presence of a basic acid-binding agent in an appropriate aprotic solvent (preferably pyridine or another tertiary amine capable of binding acids).

According to variant (e) of the process the appropriately substituted 2-hydroxy-phenyl-benzyl ketone is reacted with organic acid anhydrides in the presence of a basic catalyst. The anhydrides of acetic, propionic or benzoic acids can be used as organic acid anhydrides. The anhydride is heated in the presence of a basic catalyst, preferably of the alkali metal salt of the acid component of the anhydride or of a tertiary amine, in the absence of solvents or in an aprotic solvent of higher boiling point such as pyridine or dimethyl formamide.

In carrying out variant (f) of the process according to the invention, the ketone is reacted with N, N-dialkyl acid amides in the presence of phosphorus oxychloride, preferably in a way such that the appropriately substituted 2-hydroxy-phenyl-benzyl ketone is heated with the N, N-dialkyl acid amide (dimethyl formamide, dimethyl acetamide) and phosphorus oxychloride, and using the N, N-dialkyl acid amide (dimethyl acid amide itself as a solvent).

In carrying out variant (g) of the process, 2-hydroxy-isoflavanones of the formula IV are dehydrated by heating alone or in an acidic medium in a polar solvent.

In the course of the process according to the present invention, in the first step, from the compounds of the formula III or IV derivatives can be obtained in which the substituent $R^6$ is not the $R^5$ group desired to be present in the end product. In these cases the $R^6$ group may be converted into and $R^5$ group. This operation can be carried out by the partial or complete alkylation of mono- and poly-hydroxy-isoflavones, respectively. The alkylation can be preferably performed with alkyl or substituted alkyl halides, alkyl sulfates, olefins and epoxides, preferably in a way such that the alkylating agents are heated with the isoflavones to be alkylated, in appropriate solvents, ketones, dimethyl formamide or ethers having a longer carbon chain, in the case of haloid compounds preferably in the presence of an acid-binding agent such as alkali carbonate, and in the case of alkyl bromides and alkyl chlorides preferably in the presence of an alkali iodide.

The mentioned operation can also be carried out by the partial or complete deacylation and, respectively, the partial or complete dealkylation of acyloxy- and poly-alkyloxy-isoflavones. Acyloxy- and polyacyloxy isoflavones are formed when the procedure of variant (e) is carried out with di- and polyhydroxy-phenyl-benzyl ketones which carry a hydroxy group in the 2 position. Deacylation is preferably performed in an acidic or alkaline medium in the presence of a polar solvent.

The operation can also be performed by the decarboxylation of isoflavone-2-carboxylic acids. Isoflavone-2-carboxylic acids are formed in variant (d) of the process and their decarboxylation may be preferably carried out by heating them in the presence of catalysts such as powdered copper or in the absence of catalysts.

On the basis of the abundant literature on studies concerning the oestrogenic properties of isoflavones and of the data of our research in this field, we were able to produce isoflavone compounds which are devoid of any oestrogenic effect. As described in the above-mentioned application certain types of isoflavone derivatives show a marked weight yield increasing effect which essentially exceeds that of isoflavone compounds possessing definite oestrogenic effects, and this weight yield increasing effect is associated with a reduction or complete absence of oestrogenic effect.

Thus, in the course of our observations in discovering in a field still not described in literature, i.e. in the group nonoestrogenic isoflavones, a very interesting novel biological effect, that of increasing the weight yield, has been found. Beside this action, a significant part of the compounds show anatoxic effects free of androgen effects as well (proved by N-retention and by the musculus levator test or by measuring the skeletal muscle increasing effect). The major part of these compounds were new compounds not synthesized before. It must be emphasized that certain members of this group of compounds show weight-yield increasing effects exceeding all effects of this type known and are at the same time practically in other respects innocuous to the living organism ($DL_{50}$ > g per kg of body weight); the effect is substantially independent of the composition of the feed. The compounds are relatively easily and economically synthesizable on an industrial scale, they are stable, limitlessly storable substances free from taste and odor.

Concerning the effect of the compounds the pharmacological tests given below are of special interest.

Test of anabolic effect: The investigation was carried out with castrated rats by means of the musculus levator ani test and vesicula seminalis test. The preparations were administered orally for a period of three weeks. The tests were performed by the method of Eisenberg and Gordan (Eisenberg, E., Gordan, G. S. J.: J. Pharmacol. 99, 38, 1950). In addition to that, also the weight of the prepared diaphragm of the animals was established. According to these tests, the weight of musculus levator ani rose by a Student significance of p 0.01, the weight of vesicula seminalis did not increase while the weight of the prepared diaphragm of the animals increased by a Student significance of p 0.05. On the basis of these results the preparations proved to possess the anabolic activity free from androgen effect.

During the tests, a total of 30 mg/kg of active ingredient was administered to the animals.

The investigation of nitrogen retention was carried out also with rats. Under a systematic treatment, the nitrogen excretion of the treated animals decreased on the 20th and 30th day, respectively, by a significance of p 0.05.

The result of these investigations similarly pointed to the anabolic effect.

Examinations with S-35 labelled methionine show that under the effect of treatment, increased methionine incorporation takes place in the muscle tissues of the treated animals.

The muscle-activity-increasing effect was investigated by the forced swimming test of rats. The animals were forced to swim in water of 29 deg. C with a load of 3g/100 g body weight. The calorie content and quantity of feed administered was the same as with control animals.

The difference between the periods of forced swimming until exhaustion of the control animals and the animals treated for 45 days and forced to swim daily was 33 minutes (the control animals were subjected to identical treatment with the exception of the active ingredient), i.e. the swimming period (performance) of the control animals increased from 166 to 196 minutes while that of the treated animals from 162 to 225 minutes.

These experiments were carried out by administering daily doses of 5 mg/kg of body weight.

In further experiments we succeeded in partially suppressing the catabolic effect of cortisone with these compounds, and proved that identical doses of anabolic steroids do not exert anabolic effects stronger than that of the invented compounds.

On examining the data of the analysis of body weight it was found that the weight increase of the muscle tissue was specifically greater than that of the fat tissue, and that fat content of the muscle tissue decreased, while that of proteins rose.

The acute toxicity tests proved the full innocuity of the preparation. During a 48 hour period of observation no mice died on administering orally 4000 mg/kg of body weight doses or subcutaneously 3500 mg/kg doses. In rat tests, no perceptible alterations were observed during a 48 hour period, after administering orally or subcutaneously 3500 mg/kg of body weight doses.

On dogs, no alterations were observed during a week of administering 3500 mg/kg body weight doses.

The subacute toxicity tests were performed on rats. When administering daily doses of 200 mg/kg of body weight and 500 mg/kg of body weight orally, no alterations could be observed after one month of test period.

Similar results were obtained in the subacute tests carried out with mice.

As regards chronic toxicity up to the present, after three-month chronic toxicity tests have been completed. After administering daily 100 mg/kg of body weight for three months to male and female rats, no perceivable alterations were observed (full blood investigation, histological and other clinical tests).

Similiarly, negative results were obtained in the toxicity tests with dogs after the first 3 months of observation (here the doses were 20 mg/kg of body weight and 50 mg/kg of body weight).

The oestrogenic effect of the compounds was investigated by the uterus test on infantile mice, after oral and subcutaneous administration. No oestrogenic effects of the compounds were observed.

After administering daily 5 mg/kg of body weight of preparations to chickens for 30 days, the endocrine glands of the experimental animals were subjected to a detailed histological investigation. No perceivable alterations were observed.

The weight yield increasing effect induced by doses of 2 g/100 kg of feed was in the various animal species as follows:
  8 to 15% in calves
  7 to 10% in cattle
  7 to 10% in hogs
  8 to 20% in poultry
  10 to 20% in rabbits
  8 to 12% in guinea pigs The periods of administration varied from one to four months, depending on the animal species and conditions of breeding. The treated animals did not obtain greater amounts of feed than the control tests during the treatment period. Moreover, in several cases some saving of feed could be attained quite independently of the weight yield increasing effect.

It was observed during the treatment period that the experimentally treated animals showed an increased vitality, and the weight increase was mainly due to an increase of muscle mass. This was particularly evident in pig fattening trials when, in the case of bacon pigs, the ratio of pigs of class A, low in fat, was significantly higher.

In the rats, also the effect exerted on the reproductive organs was separately examined. The capability of reproduction and the number of brood were in case of males and females pretreated with the active ingredient the same as that on untreated controls.

In an investigation on the uptake and excretion of C-14 labelled isoflavones it was found that the uptake is rather quick in both oral and intramuscular administration. After oral administration, half of the ingredient introduced was excreted with urine while the other half with feces.

In a number of organs, activity detectable by radiography was present 48 hours after completion of the treatment.

OBJECTS OF THE INVENTION

It is an object of the present invention to extend the principles originally set forth in application Ser. No. 146,773 now U.S. Pat. No. 3,833,730.

Another object of the invention is to provide nonoestrogenic compounds having anabolic activity and useful in promoting weight gain.

Still another object of the invention is to provide a method of treating human patients to promote weight gain.

Yet another object of the invention is to provide a composition for the treatment of subjects to achieve anabolic activity.

DESCRIPTION OF THE INVENTION

This application deals with compounds within the generic definition of formulas I and II which also conform to the formula

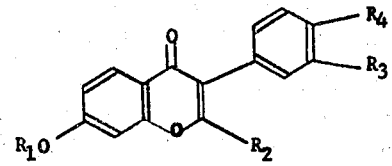

wherein $R_1$ is halosubstituted, nitrosubstituted or unsubstituted propyl, amyl or benzyl, $R_2$ is hydrogen, methyl or carboxy and $R_3$ and $R_4$ are the same or different and are hydrogen, methoxy or nitro.

These compounds include compounds in which the group at the 7 position of the isoflavone derivative is:
  propyloxy,
  amyloxy,
  benzyloxy,
  chlorobenzyloxy,
  nitrobenzyloxy, or
  chloropropyloxy;
the group at the 2 position is:
  hydrogen,
  methyl, or
  carboxyl; and
the group at the 3' and 4' positions are:
  hydrogen,
  methoxy, or
  nitro.

Preferably the halo substituent is chloro and the $R_3$ and $R_4$ members (at the 3' and 4' positions) are hydrogen or nitro. Where $R_1$ is propyl, the branched alkyl (isopropyl) is preferred.

The following compounds have been found to be most effective for the present purposes:
  7-isopropoxyisoflavone,
  7-(4-chlorobenzyloxy)-isoflavone, and
  7-isopropoxy-4'-nitroisoflavone.

These compounds, which can be made by the process variants (a) to (g) set forth previously, have the structural formulae:

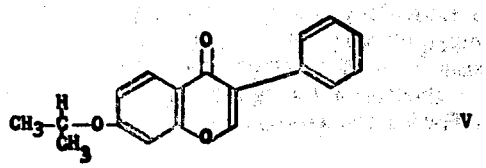

7-isopropoxyisoflavone

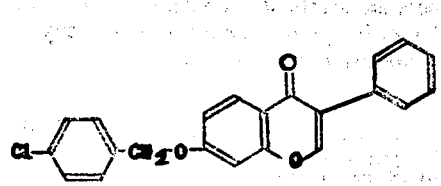

7-(4-chlorobenzoxy)-isoflavone

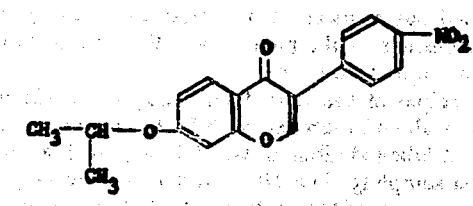

7-isopropoxy-4'-nitro-isoflavone

The latter compounds have been found to be useful as anabolic agents upon human patients.

For use in human therapy the compounds (individually or in a mixture of two or more) may be processed by the known methods of drug production to form tablets, dragees, powder mixtures, solutions, emulsions or suspensions, primarily for oral administration, in combination with or without vitamin-containing mixtures. The daily dosage is 0.2 to 100 mg/kg of body weight and parenteral or rectal administration may also be used.

SPECIFIC EXAMPLE 27 g of 2-hydroxy-4-isopropyloxy-phenyl-benzyl ketone, 22 g of ethyl orthoformate and 5 g of morpholine are boiled for 8 hours in 200 ml of dimethyl formamide. The ethanol formed during the reaction is removed through a fraction head. Then the major part of solvent is distilled off in vacuum and the residue is diluted with dilute aqueous hydrochloric acid. The crude product is filtered and recrystallized from acetone, yielding 24 g of 7-isopropyloxy-isoflavone of m.p. 115°–117°C.

Using a similar method, 7-n-amlyoxy-isoflavone, m.p. 142°–143°C is prepared from 4-n-amyloxy-2-hydroxy-phenyl-benzyl ketone (m.p. 72°–75°C).

EXAMPLE 2

28.6 g of 2-hydroxy-4-isopropyl-phenyl-benzyl ketone or 2-hydroxy-4-n-amyloxy-phenyl-benzyl ketone are dissolved in 50 ml of anydrous ether, 25 g of zinc cyanide are added, and the solution is saturated, under cooling, with dry hydrogen chloride gas. After allowing the mixture to stand for 24 hours, the solvent is decanted from the separated oil, the oil triturated with ether, the ether is decanted, and the residue is heated with 1000 ml of water for 30 minutes on a water bath. The product which precipitates on cooling is filtered, and recrystallized from a mixture of methanol and acetone, thus 7-Isopropyloxy-isoflavone and 7-n-amyloxy-isoflavone, already described in Example 1, is produced.

EXAMPLE 3

A solution of 18 g of 2-hydroxy-4-isopropyloxy-phenyl-benzyl ketone in 150 g of ethyl formate is added in small portions under cooling to 9 g of powdered sodium. After allowing the reaction mixture to stand for some hours, it is treated with ice water containing hydrochloric acid, the ethyl formate is distilled off, the residual aqueous mixture is boiled for an hour, and the product precipitated on cooling is recrystallized from acetone, thus 11 g of 7-isopropyloxy-isoflavone are obtained, m.p. 115°–117°C. In a similar way, 7-n-amyloxy-isoflavone already described in Example 1 can also be produced.

EXAMPLE 4

To a solution of 13.5 g of 2-hydroxy-4-isopropyloxy-phenyl-benzyl ketone in 120 ml of pyridine, 11 ml of ethyloxyalyl chloride are added under cooling. After allowing the reaction mixture to stand for a day, it is diluted with water, extracted with chloroform and repeatedly shaken with a 10% aqueous hydrochloric acid solution. On evaporating the solution, the residue is treated for 5 hours with a mixture of 100 ml of methanol and 50 ml of a 10% aqueous solution of sodium hydroxide, the methanol is distilled off, and the aqueous solution is acidified. The product is filtered, thoroughly dried and, after addition of 5 g of powdered copper, heated to 250°C. On completion of the evolution of gas, the residue is crystallized from methanol, yielding 5 g of 7-isopropyloxy-isoflavone, m.p. 116°–117°C.

EXAMPLE 5

28.6 g of 2-hydroxy-4-isopropyloxy-phenyl-benzyl ketone or 2-hydroxy-4-n-amyloxy-phenyl-benzyl ketone and 25 g of anhydrous sodium acetate are boiled for 14 hours with 120 ml of acetic anhydride under a reflux condenser. The reaction mixture is poured into water, allowed to stand for and the precipitated substance is recrystallized from a mixture of methanol and acetone, yielding 7-isopropyloxy-2-methyl-isoflavone, m.p. 152°–154°C and 7-n-amyloxy-2-methyl-isoflavone, m.p. 87°–89°C.

EXAMPLE 6

16 g of phosphorus oxychloride are mixed with 50 ml of dimethyl formamide with cooling. After 15 minutes, 27 g of 2-hydroxy-4-isopropyloxy-phenyl-benzyl ketone are added, and the mixture is boiled for 18 hours under a reflux condenser. On dilution with water, the precipitate is filtered dried, boiled with 200 ml of methanol, and the methanolic extract is evaporated to a small volume. On recrystallizing the separated crude product from acetone, 10 g of 7-isopropyloxy-isoflavone described in Example 1 are obtained.

EXAMPLE 7

23.8 g of 7-hydroxy-isoflavone in 200 ml of anhydrous acetone are boiled, under stirring, with 18 g of n-amyl bromide, 18 g of potassium carbonate and 1 g of potassium iodide for 72 hours under reflux condenser. The inorganic salts are removed by filtration, the filtrate is subjected to steam distillation in order to remove acetone and excess reagent, the precipitate is filtered and recrystallized from acetone, yielding 7-n-amyloxy-isoflavone, m.p. 120°–122°C. In s similar way, also 7-isopropyloxy-isoflavone, 7-isopropyloxy-2-methyl-isoflavone, and 7-n-amyloxy-2 methyl-isoflavone, and 7-n-propyloxy-isoflavone, m.p. 162°–164°C,
7-n-propyloxy-2-methyl-isoflavone, m.p. 120°–122°C,
7-benzyloxy-2-methyl-isoflavone, m.p. 139°–141°C,
7-(4-chlorobenzyloxy)-isoflavone, m.p. 182°–184°C,
7-(4-chlorobenzyloxy)-2-methyl-isoflavone, m.p. 154°–156°C,
7-(4-nitrobenzyloxy)-2-methyl-isoflavone, m.p. 201°–203°C, and
7-(3-chloropropyloxy)-isoflavone, m.p. 137°–138°C, can be prepared.

EXAMPLE 8

12 g of 7-hydroxy-isoflavone are boiled for 2 hours under a reflux condenser with 10 g of potassium carbonate and 9 g of isopropyl bromide in 40 ml of dimethyl formamide. On pouring the reaction mixture into water, the separated product is recrystallized from acetone, yielding 7-isopropoxy-isoflavone. In a similar way all the other isoflavone derivatives described in Example 7 can be prepared.

EXAMPLE 9

10 g of 7-hydroxy-2-methyl-isoflavone, 10 g of anhydrous potassium carbonate, 1 g of potassium iddide and 12.5 g of benzyl chloride are boiled in 200 ml of anhydrous acetone for 2 hours with stirring, under a reflux condenser. On subjecting the mixture to steam distillation, the crude product precipitating from a mixture of 100 ml of methanol and 40 ml of acetone, yielding white needle crystalls of 7-benzyloxy-2-methyl-isoflavone, m.p. 139°–141°C.

EXAMPLE 10

10.5 g of 7-hydroxy-isoflavone in 200 ml of anhydrous acetone are boiled for 2 hours with 11.8 g of p-nitrobenzyl iodide in the presence of 5.7 g of anydrous potassium carbonate under a reflux condenser. On distilling off about half of the volume of acetone, the residue is poured into 1000 ml of water. The precipitating crude product is subjected to suction and recrystallized from glacial acetic acid, affording light yellow plates of 7-p-nitrobenzyloxy-isoflavone, m.p. 225°–226°C.

EXAMPLE 11

The daily dosage of 7-isopropoxy-isoflavone and the compounds of formulas VI and VII may vary within wide ranges and depends on the circumstances of the particular case. If administered orally (to humans) the average daily dose may generally amount to 50–1000 mg, preferably 300–600 mg. A preferred dosage consists of 3×50 to 3×200 mg per day. A composition suitable for oral administration in tablet form has the following composition:

|  | per tablet |  |
|---|---|---|
| 7-isopropoxy-isoflavone | 0.1 | g |
| Potato starch (amylum solani) | 0.084 | g |
| Magnesium stearate | 0.01 | g |
| Polyvinylpyrrolidine | 0.006 | g |
| Total | 0.200 | g |

The tablets are stable at a temperature of 40°, 50° and 55°C. The disintegration time is 6–8 minutes. Another tablet composition is as follows:

|  | per tablet |
|---|---|
| 7-isopropoxy-isoflavone | 0.1 g |
| Avicel (Encompress) | 0.1 g |
| Total | 0.2 g |

Other anabolic isoflavones may be formulated in an analogous manner.

The following test report relates to the anabolic effect of 7-isopropoxy-isoflavone: Detailed experiments on preclinical level were carried out by using 7-isopropoxy-isoflavone. The primary object was the proving of anabolic effect on humans. Experiments were carried out by means of the most up-to-date methods. THe essence of the method was the determination of the nitrogen turn-over.

Principle of the test: After intravenous administration of albumin labelled with I-131 isotope the excretion of labelled albumin was followed with a series of blood sampling. The 50% excretion value — $T_1/2$ — characteristic of the anabolic effect of the composition. It has been found that the $T_1/2$-value has significantly shortened as a result of the administration of the anabolic isoflavone (from 8.03 days to 7.23 days) which is also indicative of the protein incorporation.

The composition has the advantage over steroidal antibiotics that in addition to the shortening of the turn-over period (i.e. increase of the albumin incorporation) it also augments the albumin level within a short time (10–15 days).

In the above test the active compound was administered in 3×–150 mg oral doses.

The tests included 10 treated and 10 control patients.

The anabolic effect of the composition was tested on thinned (asthenic), reconvalescent, dystrophic patients suffering from pathological thinness. It has been found that as a result of a treatment lasting for some weeks the patients have gained 2–3 kg of weight. According to our experiments the physical condition of the patients has also improved.

Another characteristic feature of the anabolic effect is the calcium and phosphate retention. These tests were performed on young sheep. It has been found that calcium and phosphorus retention was significantly increased by 20 mg/kg body weight dose.

The essence of the test is as follows: In animals, which were in a state of equilibrium as regards the calcium, phosphate, potassium and nitrogen turn-over, the said complete turn-over was determined prior to and after treatment. The determination of the metal ions was carried out in the fodder and feces by means of flame-photometry after decomposition, while in the urine and drinking water it was performed by means of direct flame-photometry. The inorganic phosphorus was determined, by the method of Fiske-Subbarow and nitrogen was determined according to the micro-Kjeldahl-method.

the calcium retention effect was also proved by means of the isotope method in rats.

After the above tests the composition was tested in osteoporosis of immobilisation and endocrine origin. In this test we also succeeded in proving the calcium retaining effect of the composition in a daily dosage of 300 mg per diet. The subjective complaints, pain-sensation of the patients have considerably decreased.

We claim:

1. An anabolic treatment method for human patients comprising administering to said patients in a daily dosage of 0.2 to 100 mg/kg of body weight a compound having the formula

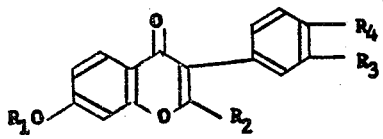

wherein $R_1$ is halosubstituted, nitrosubstituted or unsubstituted propyl, amyl or benzyl, $R_2$ is hydrogen, methyl or carboxy and $R_3$ and $R_4$ are hydrogen or nitro.

2. The method defined in claim 1 wherein said compound is selected from the group which consists of:
7-isopropoxyisoflavone,
7-(4-chlorobenzyloxy)-isoflavone, and
7-isopropoxy-4-nitroisoflavone.

3. The method defined in claim 2 wherein said compound is 7-isopropoxyisoflavone.

4. The method defined in claim 1 wherein said daily dosage is 50 to 1000 mg.

5. The method defined in claim 4 wherein said compound is administered orally in a daily dosage of 300 to 600 mg.

6. An anabolic treatment method for human patients comprising administering to said patients in a daily dosage of 0.2 to 100 mg/kg of body weight a compound having the formula:

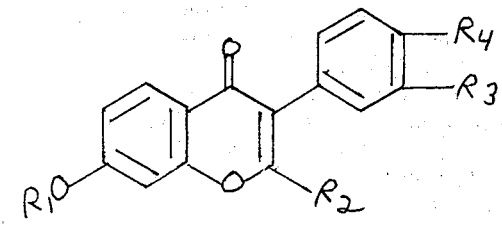

wherein $R_1$ is halosubstituted, chlorosubstituted or unsubstituted propyl, amyl or benzyl, $R_2$ is hydrogen, methyl or carboxy, and $R_3$ and $R_4$ are hydrogen, methoxy or nitro.

7. An anabolic orally administerable pharmaceutical composition which consists essentially of 0.1 part by weight 7-isopropoxyisoflavone, 0.084 parts by weight potato starch, 0.01 part by weight magnesium sterate and 0.006 part by weight polyvinylpyrrolidine.

8. An anabolic pharmaceutical composition comprising a pharmaceutically acceptable vehicle and an effective amount of a medicament consisting of a compound of the following formula:

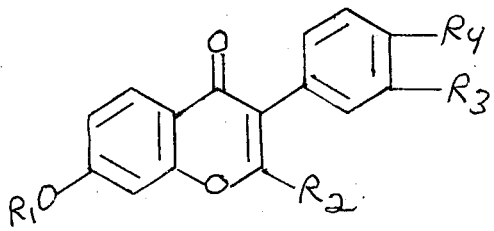

wherein $R_1$ is halosubstituted, nitrosubstituted or unsubstituted benzyl, $R_2$ is hydrogen, methyl or carboxy and $R_3$ and $R_4$ are hydrogen, methoxy or nitro.

9. An anabolic pharmaceutical composition comprising a pharmaceutically acceptable vehicle and an effective amount of a medicament consisting of a compound of the following formula:

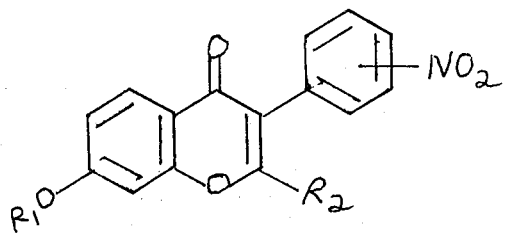

wherein $R_1$ is halosubstituted, nitrosubstituted, or unsubstituted propyl, amyl or benzyl; $R_2$ is hydrogen, methyl or carboxy.

10. An anabolic pharmaceutical composition comprising an effective amount of a pharmaceutically acceptable vehicle and a medicament consisting of a compound of the following formula:

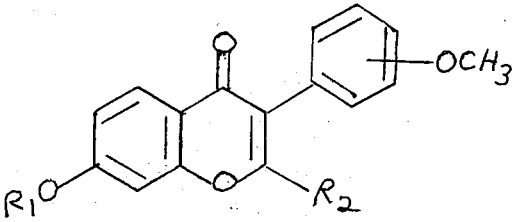

wherein $R_1$ is halosubstituted, chlorosubstituted or unsubstituted propyl, amyl or benzyl and $R_2$ is hydrogen, methyl or carboxy.

* * * * *